United States Patent [19]

Breuer

[11] 4,278,659
[45] Jul. 14, 1981

[54] HAIR SETTING AND BODYING COMPOSITION AND METHOD

[75] Inventor: Miklos M. Breuer, Rockville, Md.

[73] Assignee: The Gillette Company, Boston, Mass.

[21] Appl. No.: 83,137

[22] Filed: Oct. 9, 1979

Related U.S. Application Data

[63] Continuation of Ser. No. 972,597, Dec. 22, 1978, abandoned.

[51] Int. Cl.$^3$ ............................ A61K 7/09; A61K 7/11
[52] U.S. Cl. ............................................. 424/71; 132/7
[58] Field of Search ........................................... 424/71

[56] References Cited

U.S. PATENT DOCUMENTS

| | | | |
|---|---|---|---|
| 2,519,842 | 8/1950 | Maaskant | 528/155 |
| 2,552,129 | 5/1951 | Windus | 8/94.24 |
| 2,552,130 | 5/1951 | Windus | 8/94.14 |
| 3,242,118 | 3/1966 | St. Clair et al. | 528/155 |
| 3,661,161 | 5/1972 | Kalopissis et al. | 424/DIG. 2 |

OTHER PUBLICATIONS

"The Merck Index", 9th Edition, No. 7951, (1976).

*Primary Examiner*—Dale R. Ore
*Attorney, Agent, or Firm*—Leonard J. Janowski

[57] ABSTRACT

Compositions and method for imparting shampoo resistant body and settability to human hair comprising the application of an aqueous solution containing a precondensate of glyceraldehyde and resorcinol under conditions promoting in situ polymerization.

12 Claims, No Drawings

HAIR SETTING AND BODYING COMPOSITION AND METHOD

This is a continuation of application Ser. No. 972,597, filed Dec. 22, 1978, now abandoned.

FIELD OF THE INVENTION

The field of the invention comprises broadly the treatment of natural and artificially produced protein fibers to permit the natural fiber configurations to be altered in manners not possible with the untreated fibers. Fiber types include natural fibers such as human hair, animal hair, wool and silk, and artificial fibers such as those spun from soybean protein, casein, zein or gelatin solutions.

More narrowly, the field of invention includes the treatment of human hair on the head to strengthen it and to impart and maintain a desired fiber configuration or array. Such treatments include curling, setting, permanent waving, straightening, and the repair of fiber damage.

DESCRIPTION OF THE PRIOR ART

The simplest, most commonly used and undoubtedly the oldest method of altering the natural configuration of hair on the human head is to wet with water, arrange the fibers in an altered configuration, allow the hair to dry and comb it into a desired style. This age old practice is ideally satisfactory for the purpose of temporarily altering hair styles genetically bestowed, but falls short of the mark when one wishes to achieve a new look without the need for the ritual of daily water setting.

The temporary nature of water setting is, as is well known, due to the presence in the structure of hair keratin of both covalent disulfide bonds which are not affected by water setting and secondary bonds including hydrogen bonds and salt linkages which are readily broken and reformed in new locations in the presence of water. In the presence of a moist atmosphere, as on a humid day or as the result of scalp perspiration, a temporarily set hair fiber will tend to return to its original configuration by virtue of the influence of the covalent bonds.

One way of overcoming the effects of these bonds is to temporarily break them by the application of a suitable reducing agent after which the fibers are arranged in an altered configuration and the disulfide linkages rebuilt at new sites within the fiber. The end result is a molecular structure in which the covalent bonds serve to maintain a modified hair style, working with rather than against the water modifiable secondary bonds. This chemical approach to the problem is the basis for the various "permanent waving" processes and products available for self-application or as beauty shop treatments.

Long before the age of chemistry had dawned and the structure of hair keratin had been unravelled, attempts had been made to use mechanical means to reduce the propensity of human hair to revert to its natural form in humid circumstances. Where the ancients used mud and various naturally occurring gums and resins to reinforce an artifically constructed hair style, modern personkind applies a solution of synthetically produced polymer, usually as a fine spray, which serves to mechanically fix the fiber array by partially coating the surfaces of individual fibers and by forming interfiber bridges of dried polymer. Since products of this type do not react chemically with the hair keratin to which they are applied, they may be used as often as desired without causing damage. This is fortunate because mechanical disturbance of the hair by combing, wind action, or fondling will reduce the effectiveness of the product.

Inspired by the physical-chemical characterization of the structure of keratin and the possibility that polymer chemistry might be used to permanently alter the water setting behavior of keratin fibers, investigators have proposed that such fibers, including hair, be treated with a variety of monomeric species under conditions such that in theory the monomers can penetrate into the fiber structure before undergoing polymerization. Depending upon the amount of polymer apparently induced to form in situ, the resulting fiber should have properties related to both unmodified keratin and a fiber composed entirely of the synthetic polymer.

While the more recent investigators appear to have devoted their efforts to the development of ways to use various vinyl polymers in addition polymerization processes, the earlier work involved the exploration of the condensation polymerization of hydroxyaromatic compounds with aldehydes, primarily formaldehyde. These systems, while capable of endowing hair with improved set holding qualities, have never been successfully commercialized owing to a number of shortcomings, notably, the medical unacceptability of formaldehyde, the complexities of the process, the harsh feel the hair is left with after the treatment owing to polymeric surface deposits and hair discoloration problems.

SUMMARY OF THE INVENTION

As a result of our explorations of the use of in situ condensation polymerization reactions in the modification of keratin fiber behavior, we have unexpectedly and gratifyingly found that hair tresses treated with aqueous mixtures containing a precondensate of glyceraldehyde and resorcinol exhibit excellent and lasting set holding to hair with significant increases in body. These improved properties are resistant to high humidity conditions and removal by normal shampooing. The treated hair is similar to intact hair in feel, luster, mechanical strength, and wet and dry combing characteristics. The stability of the hair color to light exposure appears to be at least equal to that of intact hair.

DETAILED DESCRIPTION OF THE INVENTION

The primary object of this invention is to provide a treatment which will impart to human hair the property of multistylability. Multistylability is essentially a combination of two properties: a capability for maintaining an imparted set for a considerable length of time even under conditions of high humidity and the capability of being restyled into new configurations after wetting of the hair. Once restyled, multistylable hair will maintain its new configuration even after exposure to high humidities. In this manner, it differs from both intact and permanently waved hair inasmuch as either will revert at high humidities to an original style, i.e. intact hair to its natural configuration and waved hair to the one which has been imparted during the permanent waving process.

In the practice of our invention, hair which may have been previously washed is treated with an aqueous solution containing a precondensate of glyceraldehyde and resorcinol. After the treating solution has had a chance to penetrate and further condense within the hair fibers, the hair tresses take on the attributes of multistylability as described above. Such treated tresses can be shampooed and reset on rollers through several cycles without losing the imparted multistylability, exhibiting improved set retention when compared to intact, water set tresses.

Tresses of straight hair treated in accordance with our invention when wetted and set straight as for example by combing out and drying while hanging free with a weight attached, remain straight, even under conditions of high humidity in contrast to intact curly hair or permanently waved tresses which revert to curly configurations upon wetting.

Our studies have shown that it is possible to bring about a limited amount of in situ polymerization of glyceraldehyde and resorcinol by immersing hair in an aqueous composition prepared by dissolving the monomers in water at room temperature followed by heating of the saturated hair fibers. The result, however, is of marginal practical utility in that the imparted set holding improvement is of a low magnitude and exhibits poor resistance to shampoo removal. Moreover, the treated tresses are often discolored, confirming the experiences of investigators described in the prior art.

We have discovered that these problems can be solved if prior to the application to the hair the glyceraldehyde and resorcinol are heated together in the presence of boric or silicic acid to bring about the partial conversion of the monomeric species to a low molecular weight, oligomeric precondensate species. The conditions under which the precondensate is formed and proportions of the reactant species are very important in achieving an optimum result.

To form the precondensate referred to above, we prefer to heat an aqueous solution containing glyceraldehyde, resorcinol and boric or silicic acid. In investigating the effects of varying the ratio of glyceraldehyde to resorcinol in the practice of our invention, we have found that the optimum molar ratio is about 1:1 with the preferred range being 4:1 to 1:4. It is possible, however, to achieve useful set holding improvements employing ratios ranging from 19:1 to 1:19. While, in general, the effectiveness of the treatment increases with increasing concentration of glyceraldehyde and resorcinol, we prefer to use about 10%. Little additional improvement is realized by employing higher concentrations although as much as 20% by weight combined glyceraldehyde and resorcinol in the solution may be used to form the precondensate. It is possible to use as little as 0.5% by weight combined glyceraldehyde and resorcinol and still achieve a useful result.

The proportional relationship between boric or silicic acid and glyceraldehyde has also been found to be important in achieving an optimum result. Whereas a 1:1 molar ratio of glyceraldehyde to acid has been found to be best, a range of ratios from 4:1 to 1:1.5 can be used in the practice of the invention.

We have also found that the result can be further improved if the pH of the reactant mixture prior to reflux is reduced by the addition of an acid stronger than the boric or silicic acid component. While our studies have shown the pH reduction by the addition of any stronger acid, organic or inorganic, is advantageous, we prefer to use hydroxycarboxylic acids such as tartaric, mandelic, salicylic, and especially citric acid. The amount of strong acid used should be sufficient to reduce the pH to about 1.6 to maximize the enhanced result. We have found that if additional acid is added to lower the pH significantly below 1.6, there may be a diminution of the resulting set holding. However, even at much lower pH levels, the acid provides an enhanced result when compared to a composition in which the pH has not been reduced below the self pH of the aqueous glyceraldehyde, resorcinol mixture, containing only boric or silicic acid.

In forming the glyceraldehyde-resorcinol precondensate referred to herein, we prefer to reflux the aqueous mixture of glyceraldehyde, resorcinol, acid (boric or silicic) and pH adjusting acid for about 90 minutes. Heating for a longer period of time appears to reduce efficacy, probably by the formation of an increased proportion of higher molecular weight species which are not able to penetrate hair fibers as readily as the lower molecular weight precondensate species formed during a shorter reflux. It is, however, possible to reflux for 24 hours or longer and still see a practically useful result. Such long reflux time, however, may result in the formation of undersirable precipitates in the reaction mixture which should preferably be removed before application to the hair.

In product applications where it is desirable to have the user of the composition prepare it freshly before application to the hair, a useful amount of precondensate can be formed by simply dissolving the active ingredients in boiling water and waiting a few minutes for the resulting solution to cool to body temperature before application.

For the purposes of ease of application and to enable the user to apply enough of the treating composition to the hair to insure the optimum result, any cosmetically acceptable thickener may be added which is non-reactive with the other ingredients and stable at the pH levels at which the invention is practiced. We prefer to use approximately 1% by weight guar gum which is added after refluxing the other ingredients.

In applying the compositions of this invention to the hair, it is desirable to first shampoo the hair with any good quality commercially available product. After shampooing and rinsing, the hair may be towel dried, if desired. The treating composition, which should be applied to the hair in a quantity sufficient to saturate it, may be applied in any convenient fashion such as direct application from a plastic squeeze bottle or by dabbing with a saturated sponge or cotton applicator.

Following application of the treating composition to the hair, it is necessary to permit it to diffuse through the fibers for 15 to 60 minutes. During this period, it is desirable to wrap the hair in a towel or plastic or other turban to reduce evaporative cooling and as an aid in retaining heat produced by the scalp. Externally applied heat as from a hair dryer, may also be employed during the diffusion step.

After the diffusion step, the hair should be thoroughly rinsed, this time to remove any undiffused treating composition from the individual fibers. Following towel drying of the treated hair, it is then preferably heated to complete conversion of the glyceraldehyde-resorcinol precondensate to the final higher molecular weight condensate product which imparts the desired mechanical properties to the modified hair fibers. This can be accomplished conveniently by wrapping the towel dried hair on conventional hair setting curlers followed by drying with either a helmet-type or hand-held hair dryer. The diameter of the rollers employed will determine in part the final styled result with smaller diameter rollers providing a tighter final curl result. We have found that rollers of ⅜ to 2 inches in diameter are suitable for the average range of hair styles.

It is also possible to bring about conversion of the precondensate by air drying or blow drying the hair in its normally straight configuration, i.e. without first wrapping it on setting rollers. In this case the dried hair can at any subsequent time be set on rollers after first wetting it with water, or it may alternatively be set dry on heated rollers.

While we have mentioned the use of heat in drying the treated hair during the condensation step, it is possible to achieve a useful result by simply allowing the treated hair, after the post-diffusion rinsing step, to dry at room temperature either in roller set or straight form. In the absence of heating, completion of the condensation step takes a longer period of time, but the end result is essentially the same.

EXAMPLE I

A glyceraldehyde-resorcinol precondensate was prepared by refluxing an aqueous solution of 5% by weight glyceraldehyde, 5% resorcinol, 1% boric acid, and 1% citric acid at the boil for one hour. The pH of the mixture was then adjusted to 3.0 by the addition of sodium hydroxide after which it was thickened by the addition of 1% of guar gum thickener (Jaquar 124-T from Stein Hall, Inc.) to provide a viscosity of 1200 c.p.s.

After cooling to room temperature, the precondensate was applied to 7-inch long tresses of intact human hair wound on ⅜-inch diameter plastic rollers employing a liquid:hair ratio of about 2:1. The rollers were then wrapped in plastic film to minimize evaporative cooling and heated in an oven at 35° C. for 30 minutes. At that time, the tresses were released from the rollers, shampooed with a commercially available anionic shampoo, reset on ⅜-inch diameter rollers and dried in an oven at 35° C. for 30 minutes.

After removal of the rollers and combing through of the treated tresses, the resulting curl was evaluated by hanging the tresses in a chamber maintained at 21° C. and 65% relative humidity and measuring tress length as a function of time. After 18 hours, comparison of the treated tresses with untreated controls which had been set with water showed a 61% improvement in the level of curl retention.

EXAMPLE II

The precondensate composition described in Example I was evaluated on human subjects as follows.

The hair of each subject was shampooed with a commercially available anionic shampoo and towel dried after which 70 cc of the test composition was applied to one-half of the head. The other half of each head was treated with a control lotion which had a pH of 3 and contained 1% citric acid and 1% guar gum thickener. The lotions were left on the head under a plastic turban for 30 minutes before they were rinsed out, after which the hair was wet set on 1-inch diameter plastic rollers and dried under an electric hair dryer. The hair on both sides of the head was then styled by an experienced beautician.

Comparative evaluations of the result both immediately after treatment and at subsequent weekly intervals after several self-shampooings indicated a definite preference for the glyceraldehyde-resorcinol treated side for both curl holding and body. The treated side also appeared to provide acceptable hair luster and ease of combing. No discoloration of the subjects' hair was noted.

EXAMPLE III

A glyceraldehyde-resorcinol precondensate was prepared as described in Example I except that it contained 3.45% boric acid (making it equimolar in glyceraldehyde and boric acid. The pH of the composition was about 1.6.

After cooling to room temperature, the precondensate was applied to 5-inch long tresses of intact human hair employing a liquid:hair ratio of about 2:1. The tresses were then wrapped in plastic film to minimize evaporative cooling and heated in their straight form in an oven at 35° C. for 35 minutes. At that time the tresses were removed from the oven, shampooed with a commercially available anionic shampoo and set on roller frames using ⅜-inch diameter rollers yielding three undulating wave patterns after being oven-dried at 35° C. for 60 minutes.

After drying, the tresses were carefully removed from the roller frames and the resulting curl evaluated by hanging the tresses in a chamber maintained at 21° C. and 65% relative humidity and measuring tress length as a function of time.

After 18 hours, comparison of the treated tresses with untreated controls which had been set in roller frames with water showed improvement in the level of curl retention of well over 200%. After five additional shampoos with a commercially available anionic shampoo, the curl retention improvement was still about 80%.

EXAMPLE IV

The treatment set forth in Example I was repeated except that tresses of one-time bleached human hair were used in place of intact hair.

After 18 hours comparison of the treated tresses with untreated controls which had been set with water showed a 40% improvement in the level of curl retention.

EXAMPLE V

A glyceraldehyde-resorcinol precondensate was prepared as described in Example III except that hydrochloric acid was used in place of the citric acid and the pH was adjusted to 1.8. In addition, the mixture was refluxed for 90 minutes. The composition was evaluated as set forth in Example III.

After 18 hours, comparison of the treated tresses with untreated controls which had been set with water showed a greater than 100% improvement in the level of curl retention.

EXAMPLES VI–XV

Compositions were prepared as described in Example V except that in each case the indicated acid was used to adjust the pH to 1.8 with the following results.

| Example | Acid Used | Percent Curl Retention Improvement |
|---|---|---|
| VI | sulfuric | 80 |
| VII | tartaric | 150 |
| VIII | succinic | 100 |
| IX | malic | 100 |
| X | gluconic | 100 |
| XI | lactic | 160 |
| XII | mandelic | > 200 |

-continued

| Example | Acid Used | Percent Curl Retention Improvement |
|---------|-----------|-----------------------------------|
| XIII | phthalic | > 200 |
| XIV | salicylic | > 200 |
| XV | acetic | 160 |

EXAMPLE XVI

A composition was prepared as set forth in Example III except that 2.2% silicic acid was used in place of boric acid and the mixture was refluxed for 90 minutes. The composition was evaluated as set forth in Example III.

After 18 hours, comparison of the treated tresses with untreated controls which had been set with water showed a 80% improvement in the level of curl retention. This improvement resisted subsequent shampooing.

I claim:

1. A hair treating composition for imparting improved setting properties comprising an aqueous solution containing about 0.5 to 20% by weight of a mixture of glyceraldehyde, resorcinol and an oligomeric precondensate of glyceraldehyde and resorcinol said composition being prepared by heating an aqueous mixture containing glyceraldehyde, resorcinol and an acid selected from the class consisting of boric acid and silicic acid, the molar ratio of glyceraldehyde to resorcinol being about 19:1 to 1:19 and the molar ratio of glyceraldehyde to said acid being about 4:1 to 1:1.5.

2. A hair treating composition as described in claim 1 in which the molar ratio of glyceraldehyde to resorcinol is about 4:1 to 1:4.

3. A hair treating composition as described in claim 1 containing, in addition, a hydroxycarboxylic acid selected from the group consisting of tartaric, mandelic, salicylic and citric acids the quantity of said hydroxycarboxylic acid being sufficient to reduce the pH of said composition to a level lower than the pH level imparted by said boric or silicic acid.

4. A hair treating composition as described in claim 1 in which the molar ratio of glyceraldehyde to resorcinol is about 1:1, the molar ratio of glyceraldehyde to said acid is about 1:1 and containing, in addition, a hydroxycarboxylic acid selected from the group consisting of tartaric, mandelic, salicylic and citric acids, the quantity of said hydroxycarboxylic acid being sufficient to reduce the pH of said composition to about 1.6.

5. A method of treating hair to impart improved setting properties comprising the application of a composition comprising an aqueous solution containing about 0.5 to 20% by weight of a mixture of glyceraldehyde, resorcinol and an oligomeric precondensate of glyceraldehyde and resorcinol said composition being prepared by heating an aqueous mixture containing glyceraldehyde, resorcinol and an acid selected from the class consisting of boric acid and silicic acid, the molar ratio of glyceraldehyde to resorcinol being about 19:1 to 1:19 and the molar ratio of glyceraldehyde to said acid being about 4:1 to 1:1.5.

6. A method as described in claim 5 in which said composition contains, in addition, a hydroxycarboxylic acid selected from the group consisting of tartaric, mandelic, salicylic and citric acids the quantity of said hydroxycarboxylic acid being sufficient to reduce the pH of said composition to a level lower than the pH level imparted by said boric or silicic acid.

7. A method as described in claim 5 in which the molar ratio of glyceraldehyde to resorcinol is about 1:1, the molar ratio of glyceraldehyde to said acid is about 1:1 and in which the composition contains, in addition, a hydroxycarboxylic acid selected from the group consisting of tartaric, mandelic, salicyclic and citric acids, the quantity of said hydroxycarboxylic acid being sufficient to reduce the pH of said composition to about 1.6.

8. A method as described in claim 6 in which the molar ratio of glyceraldehyde to resorcinol is about 4:1 to 1:4.

9. A method for the preparation of a hair treating composition for imparting improved setting properties comprising heating an aqueous solution containing about 0.5 to 20% by weight of a mixture of glyceraldehyde and resorcinol and containing, in addition, an acid selected from the class consisting of boric acid and silicic acid to form an oligomeric precondensate of glyceraldehyde and resorcinol the molar ratio of glyceraldehyde to resorcinol being about 19:1 to 1:19 and the molar ratio of glyceraldehyde to said acid being about 4:1 to 1:1.5.

10. A method as described in claim 9 in which the mixture contains, in addition, a hydroxycarboxylic acid selected from the group consisting of tartaric, mandelic, salicylic and citric acids the quantity of said hydroxycarboxylic acid being sufficient to reduce the pH of said composition to a level lower than the pH level imparted by said boric or silicic acid.

11. A method as described in claim 9 in which the molar ratio of glyceraldehyde to resorcinol is about 4:1 to 1:4.

12. A method as described in claim 9 in which the molar ratio of glyceraldehyde to resorcinol is about 1:1, the molar ratio of glyceraldehyde to said acid is about 1:1 and in which the mixture contains, in addition, a hydroxycarboxylic acid selected from the group consisting of tartaric, mandelic, salicylic and citric acids, the quantity of said hydroxycarboxylic acid being sufficient to reduce the pH of said mixture to about 1.6.

* * * * *